US008267842B2

(12) United States Patent
Schocke et al.

(10) Patent No.: US 8,267,842 B2
(45) Date of Patent: Sep. 18, 2012

(54) ERGOMETER SUITABLE FOR USE IN A MAGNETIC RESONANCE APPARATUS

(75) Inventors: Michael Schocke, Innsbruck (AT); Andreas Greiner, Rum (AT)

(73) Assignee: Ergospect GmbH, Innsbruck (AT)

( * ) Notice: Subject to any disclaimer, the term of this patent is extended or adjusted under 35 U.S.C. 154(b) by 714 days.

(21) Appl. No.: 11/911,833

(22) PCT Filed: Apr. 20, 2006

(86) PCT No.: PCT/EP2006/003639
§ 371 (c)(1),
(2), (4) Date: Dec. 14, 2007

(87) PCT Pub. No.: WO2006/111385
PCT Pub. Date: Oct. 26, 2006

(65) Prior Publication Data
US 2009/0131834 A1    May 21, 2009

(30) Foreign Application Priority Data

Apr. 20, 2005    (EP) .................................... 05008676

(51) Int. Cl.
*A63B 21/008* (2006.01)
(52) U.S. Cl. ........................................ 482/111; 482/900
(58) Field of Classification Search .................. 482/4, 5, 482/8, 9, 58, 59, 73, 111–113, 900; 73/379.07
See application file for complete search history.

(56) References Cited

U.S. PATENT DOCUMENTS

| 4,060,239 | A | * | 11/1977 | Pfleiderer et al. | ................. | 482/2 |
| 4,170,225 | A | * | 10/1979 | Criglar et al. | ................. | 600/546 |
| 4,207,680 | A | * | 6/1980 | Bell et al. | ........................ | 33/559 |
| 4,441,502 | A | * | 4/1984 | Chance | ......................... | 600/411 |

(Continued)

FOREIGN PATENT DOCUMENTS
DE    89 09 993 U1    1/1990
(Continued)

OTHER PUBLICATIONS

"Notification of the First Office Action" for related Chinese application No. 200680013534.1 filed Apr. 20, 2006; mailed Feb. 6, 2009; 11 pages.

(Continued)

*Primary Examiner* — Allana Lewin
(74) *Attorney, Agent, or Firm* — Westman, Champlin & Kelly, P.A.

(57) ABSTRACT

The present invention relates to an ergometer which is particularly suitable for examining a test person or patient in a magnetic resonance apparatus. It comprises at least one drive means which is provided essentially movably and at least one pneumatic piston/cylinder array. The drive means is provided at the piston or the cylinder and pneumatically applied pressure between the piston and the cylinder constitutes a resistance or force to be overcome by the test person or patient by operating the drive means. The resistance or the force necessary to set the drive means in motion, particularly during operation, can be controlled and/or regulated and the piston and the cylinder are sized such that an air cushion is formed between them at least during operation or when they move relative to each other. The resistance or the force necessary to operate the drive means is regulated and/or controlled automatically or electronically based on measured signals from a feedback loop during the examination of the test person or patient.

27 Claims, 2 Drawing Sheets

U.S. PATENT DOCUMENTS

Figure 1:
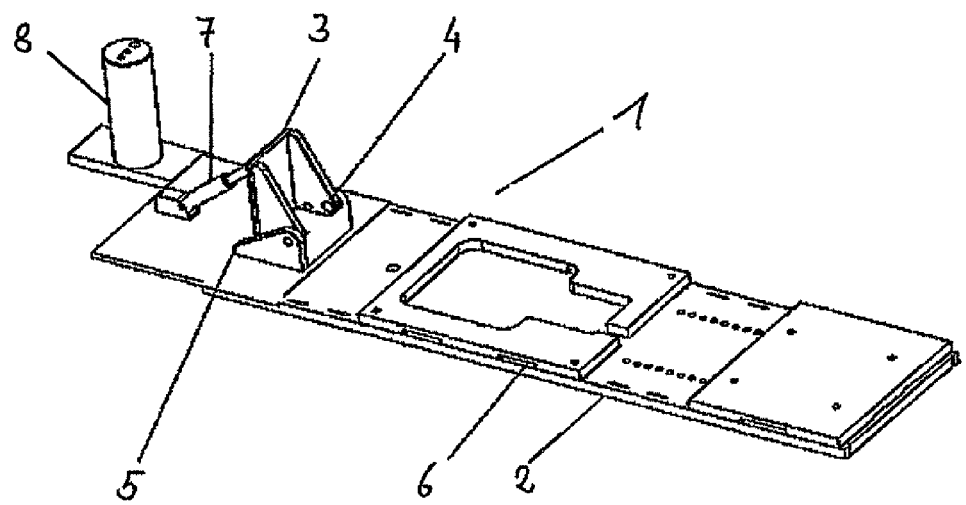

| | | | | |
|---|---|---|---|---|
| 4,461,301 A | * | 7/1984 | Ochs | 600/301 |
| 4,647,038 A | * | 3/1987 | Noffsinger | 482/106 |
| 4,835,871 A | * | 6/1989 | Pesikov | 33/1 M |
| 4,912,638 A | * | 3/1990 | Pratt, Jr. | 600/595 |
| 4,972,711 A | * | 11/1990 | Jain et al. | 73/379.06 |
| 5,081,991 A | * | 1/1992 | Chance | 600/411 |
| 5,165,278 A | * | 11/1992 | Huszczuk et al. | 73/379.06 |
| 5,257,461 A | * | 11/1993 | Raleigh et al. | 33/503 |
| 5,260,870 A | * | 11/1993 | Tsuchiya et al. | 600/595 |
| 5,401,224 A | * | 3/1995 | Tsuchiya et al. | 482/8 |

FOREIGN PATENT DOCUMENTS

WO    WO 2004/078019    9/2004

OTHER PUBLICATIONS

"A Simple Calf Muscle Ergometer for use in a Standard Whole-Body MR Scanner", Bjorn Quistorff, Steen Nielsen, Carsten Thomsen, Karl Erik Jensen, Ole Henriksen, Magnetic Resonnance in Medicine, vol. 13, No. 3, pp. 444-449, Apr. 3, 1989.

European Search Report for PCT/EP2006/003639.

* cited by examiner

ERGOMETER SUITABLE FOR USE IN A MAGNETIC RESONANCE APPARATUS

The present invention relates to an ergometer and a process for operating an ergometer which is particularly suitable for examining a test person or patient in a magnetic resonance (MR) apparatus. Such examinations are carried out, inter alia, in the fields of medical diagnostics and sports science.

Exercising different muscle groups is a frequently used method to examine muscle function in the fields of sports medicine and cardiovascular medicine. What is referred to as the 31P-MRS process (Phosphorus-31 Nuclear Magnetic Resonance Spectroscopy) is a suitable examination process wherein the blood flow in a stimulated muscle is measured locally in a magnetic resonance apparatus. This way, energy metabolites in the muscle, such as for example phosphocreatine, inorganic phosphate or adenosine triphosphate, can be measured quantitatively. By means of the 31P-MRS process it is also possible to record the energy metabolites when exercising the muscles of the calf. Initially, there is a decrease in phosphocreatine when the muscle is exercised to a certain degree until the oxygen supply in the muscle is raised to such an extent that the increased energy requirements can be met by the oxidative metabolism alone. In that case, the phosphocreatine breakdown reaches an equilibrium state. If due to a stenosis in a supplying blood vessel the blood flow and thus the oxygen supply cannot be increased to meet the demand, the phosphocreatine decreases progressively.

The use of an ergometer in a strong magnetic field is problematic since many components have to be manufactured from non-ferromagnetic metals and/or wood or plastic materials so that the device can be operated in an artifact-free manner and will function correctly, e.g. in a magnetic resonance tomograph. Also, sensors and cables for measuring device parameters such as force and travel have to be provided such that they do not cause measuring artifacts. Furthermore, it has to be possible to set a defined and reproducible force, or resistance, in an ergometer which has to be overcome by a test person or patient to set a drive means, which can e.g. be a pedal, in motion. Furthermore, it is useful if during ergometry the work output can be set, measured, or calculated, and adjusted accordingly while the ergometer is operated. When using an ergometer, the test person or patient presses against a defined resistance at a set frequency, with the deflection angle of the pedal and friction playing an important role as well. The frequency is usually given by a metronome and the force is measured by means of piezo technology. In commercially available ergometers which are operated outside of magnetic fields, the force setting is automatically readjusted via a feedback control system by means of suitable electronic or mechanic devices during the operation if the test person does not maintain the frequency or angle deflection. The use of an ergometer only makes sense if such feedback control systems are in place. The ergometers suitable for use in an MR apparatus which are currently commercially available do not comprise such a feedback control system. Moreover, in the commercially available ergometers the measuring result is falsified in a non-linear manner due to frictional resistance during the motion of the drive means so that a measuring error cannot be calculated reliably.

It is therefore the object of the present invention to provide an improved ergometer, and/or an improved ergometer arrangement, which preferably overcomes the disadvantages described above.

This object is achieved by the features described in the patent claims.

The invention is based on the fundamental idea of providing an ergometer which is particularly suitable for examining a test person or patient in a magnetic resonance apparatus. The test person or patient has to apply a certain force, which can be pre-set, at a drive means in order to set a piston/cylinder array in motion. This essentially causes the piston and the cylinder to move relative to each other. The force necessary to overcome the resistance presented by the piston/cylinder array can be controlled or regulated, in particular during the motion of the drive means. This can be done manually by specialist staff or with the help of appropriate instructions e.g. from an instructing computer program wherein the instructions are essentially based on the evaluations of the measured data. Preferably, such a computer program also automatically controls the operation. Preferably, the force range is changed manually by the specialist staff and then regulated automatically in the corresponding range. The evaluation of the work output or performance by the test person is very concise since in the present invention friction loss has been minimized to a negligible value. Friction losses can essentially be avoided by providing a cushion, preferably an air cushion, in the piston/cylinder array between the piston and the cylinder at least during relative motion.

All the components used in the ergometer were examined for their suitability in an MR apparatus, and the ergometer preferably consists of non-ferromagnetic materials, such as e.g. plastics or wood, and was furthermore only processed with tools which do not cause metal abrasion on the individual components.

The resistance, or the force, that has to be overcome or applied at the drive means to set it in motion is generated by a pneumatic system in the sense of a piston/cylinder system. In addition to compressed air, which is preferred, fluids of all kinds can be used. Preferably, compressible fluids are used. The piston is constructed such that a narrow air cushion forms between the piston and the cylinder which diminishes friction to such a degree that it is negligible in the calculation of the work output. An air vessel is provided between a compressed air inlet and the cylinder so that air pressure can be controlled or regulated infinitely at any time, even during the measurement. A computer-controlled control system is preferably used for this purpose, which is operated outside of the MR apparatus forming the Faraday cage. Thus, no electronic device is present inside or close to the MR tube in order not to affect the measuring results. The control module comprises a pressure sensor and a pressure regulator as well as a computer with the appropriate software.

The work output of the exercising muscles can be regulated in particular by the pressure in the cylinder, the depth of the piston's submergence into the cylinder and the frequency of the plantar flexion. The actual depth of the piston's submergence into the cylinder is measured; this will be explained in more detail in the description of the embodiments. The frequency is given by a metronome which provides different frequencies, whereby the test person or patient should follow the beat of the metronome when operating the ergometer. In addition to the frequency and the air pressure, the depth of the piston's submergence into the cylinder is also preferably infinitely variable. An appropriate program calculates the various parameters at a desired work output in watt or the watt number based on set parameters.

In another preferred embodiment of the ergometer as a pedal ergometer, the test person or patient preferably lies on his/her back during the measurement with his/her foot attached to a pedal with two straps. Furthermore, additional strap fixations are provided in the calf area and the shoulders in order to avoid motion artifacts. The fixation of the upper body can be adjusted to the height of the patient so that plantar flexion can be carried out to a pre-set stop and a full extension of the knee joint, respectively. A measuring coil is placed directly under the muscle or muscle group to be measured, preferably the muscles of the calf. In order to optimize the measuring result, the calf is placed in the middle of the measuring coil so that the distance between calf and measuring coil is minimized. Preferably, only one calf is measured in order to make use of the intensity of the measured signal in the center underneath the calf and thus reduce the measuring time. This is furthermore advantageous because no measuring artifacts from a second calf affect the result.

Another preferred embodiment of the ergometer is an arm ergometer wherein the mechanism of the arm ergometer corresponds to that of the pedal ergometer. Instead of leg muscles, the arm muscle to be measured, e.g. the brachial or the antebrachial muscle, is placed in an appropriate position relative to the measuring device. In this embodiment, the test person or patient can be in a standing, sitting or lying position.

In the following, the invention will be described based on exemplary preferred embodiments with reference to the drawings.

Figure 2A:
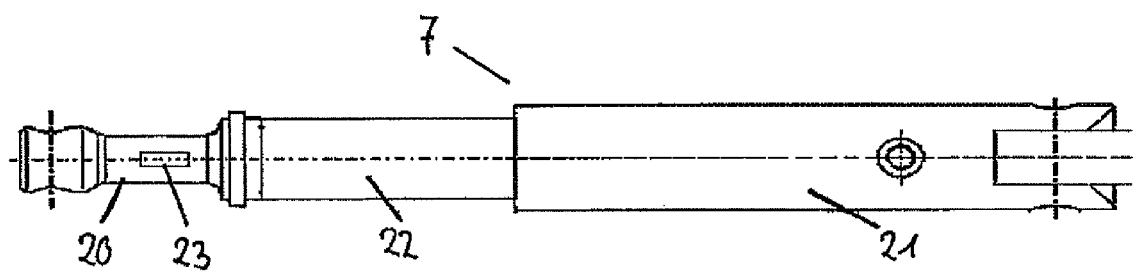
Figure 2B:
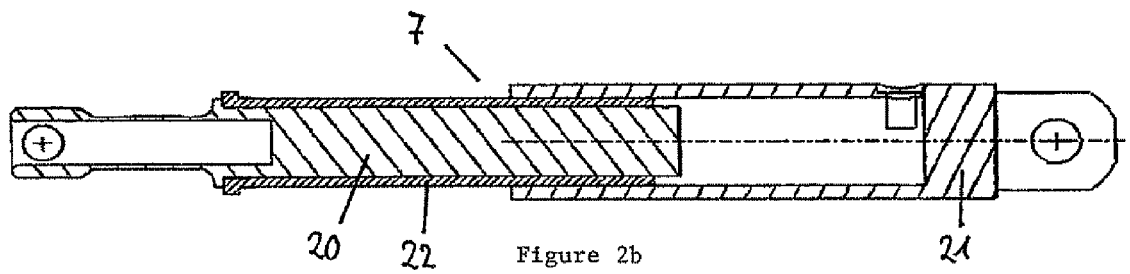
Figure 3:
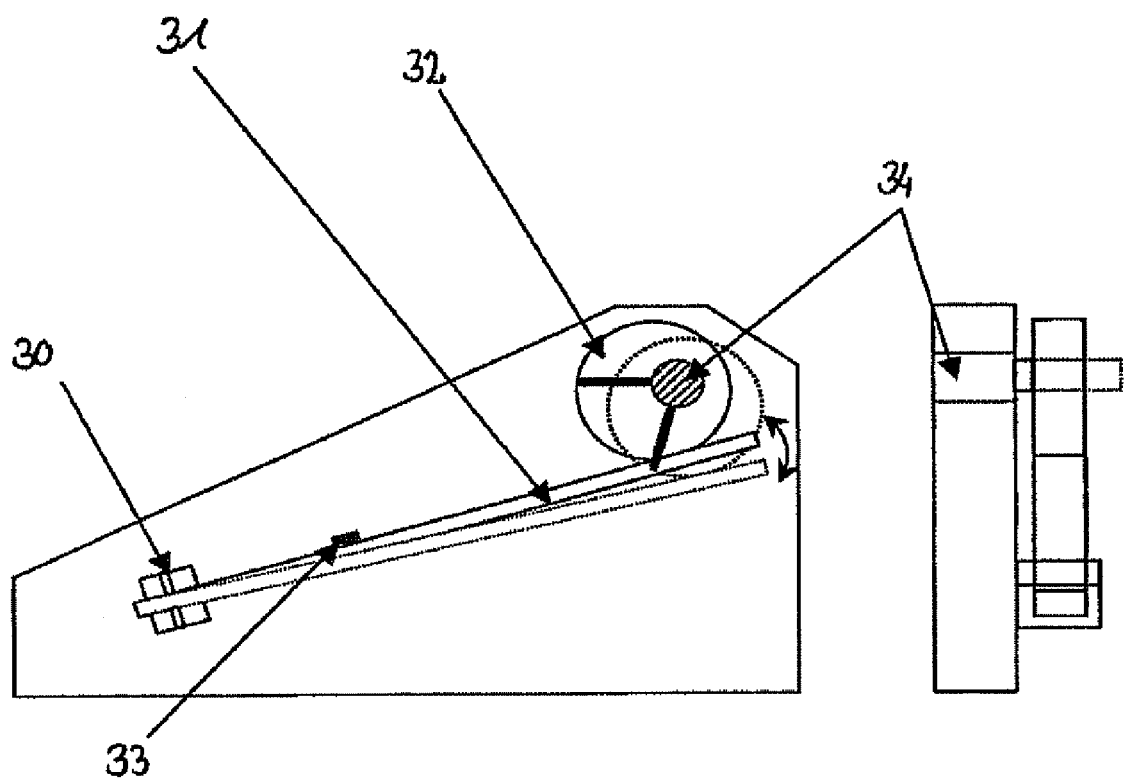

FIG. 1 shows a schematic view of an embodiment of the device according to the present invention, FIG. 2a shows a schematic view of an embodiment of the piston/cylinder array of the device according to the present invention, FIG. 2b shows a schematic sectional view of an embodiment of the piston/cylinder array of the device according to the present invention and FIG. 3 shows a schematic view of an embodiment of measuring the distance by means of a rotation angle wheel and a bending beam of the device of according to the present invention.

FIG. 1 shows a schematic perspective view of a preferred embodiment of an ergometer as a pedal ergometer 1. The components of the ergometer 1 consist of non-ferromagnetic materials so as to allow a use of the ergometer in an MR apparatus. On a base plate 2, a drive means, which in this preferred embodiment as a pedal ergometer is a pedal 3, is essentially movably provided with a fixture 5 via one or a pair of bearing pins 4, wherein the fixture 5 is firmly attached to the base plate 2. The drive means varies according to the body part to be measured, or the muscle(s) to be exercised, and is preferably designed such that when the drive means is deflected, the muscle to be measured or examined has to be exercised. For instance, the drive means can be designed such that essentially the desired muscles or muscle groups are exercised with known exercises such as e.g. butterfly, bench pressing, biceps curls, latissimus pull-down, leg extension, leg curl, leg adduction, leg press and/or cable cross. Thus, other embodiments of the drive means are e.g. handles, loops and other devices known from weight training. Preferably, the muscle to be measured essentially lies still on the measuring unit or measuring coil. For example, in the case of the pedal ergometer, the pedal 3 is therefore operated from the ankle joint in order to keep the calf as still as possible on top of the measuring coil. The drive means can preferably be attached on-center to a body part of a test person or patient to be measured so that the results supplied by the measuring coil provided in the measuring coil holder 6 are as concise as possible. A pneumatic piston/cylinder array 7 is provided between the drive means, such as e.g. the pedal 3, and a fixture on the base plate 2 such that when the drive means is deflected by a test person or a patient, the piston 20 moves relative to the cylinder 21. The pneumatically applied pressure of the piston/cylinder array 7 constitutes a resistance or force when the test person or patient operates the pedal 3. The pedal 3 preferably comprises a stop which protects the piston 20 from knocking against the bottom of the cylinder 21. This way, damage to the piston/cylinder array 7 can be prevented.

In another preferred embodiment of the ergometer according to the present invention as an arm ergometer, the ergometer is operated with muscles of the arm to be measured. The muscle(s) to be measured are positioned in a manner analogous to that described in connection with the pedal ergometer.

The pneumatically applied pressure of the piston/cylinder array 7 is supplied from a compressed air inlet connected to the cylinder 21. Preferably, an air vessel 8 is provided between the ergometer 1 and the compressed air inlet. This air vessel 8 is designed such that the air pressure applied at the piston/cylinder array 7 can be controlled or regulated via a control means, which will be explained in more detail below, and furthermore guarantees that no high or short-term load peaks result from the counter-pressure when the drive means, e.g. the pedal 3, is deflected. The force to be applied is in a range of from 50 N to 900 N, or from 100 N to 800 N, or from 200 N to 700 N, or from 300 N to 600 N and is preferably about 600 N for healthy test persons and about 300 N for patients whose movement of the body part in question is restricted.

The ergometer 1 preferably comprises a control means whose sensors and accompanying protected cables can be provided within the examination chamber of the magnetic resonance apparatus. The electronic controls of the control means are located outside of the examination chamber of the magnetic resonance apparatus. The control means regulates the air pressure at the piston/cylinder array 7 and thus the pressure exerted onto the piston 20 which constitutes the force necessary to be applied by a test person or patient in order to deflect the drive means, e.g. the pedal 3. This control means preferably comprises a computer and a computer program for controlling and/or processing acquired data.

The determination of the force to be applied at the drive means is carried out by one or several sensors provided at the piston 20 which convert a mechanical deformation to an electric signal or an electric resistance change. Preferably, a strain indicator 23 is used for this purpose. In the area of a strain indicator, the diameter of the piston 20 of the piston/cylinder array 7 is smaller than in the cylinder guidance. Furthermore, at least in the area of the strain indicator, the piston 20 can be hollow. In a preferred embodiment, the modulus of elasticity of the piston 20 is ideally 3,000 N/mm$^2$.

The resistance or force necessary to set the drive means or the pedal 3 in motion can be controlled or regulated in particular during operation. The resistance or force can be automatically or electronically regulated or e.g. controlled manually based on the signals measured during the examination of the test person or patient. Furthermore, the piston 20 and the cylinder 21 are sized such that an air cushion is formed between them at least during operation or when they move relative to each other. Due to this air cushion, the frictional resistance becomes negligible and consequently, the measured values are considerably more precise. The piston/cylinder array 7 comprises a gap between the piston 20 and the cylinder 21 of 0.02 mm to 0.05 mm, or 0.03 mm to 0.05 mm, or 0.02 mm to 0.04 mm, or 0.03 to 0.04 mm, and preferably the gap is about 0.035 mm.

Furthermore, in a preferred embodiment as pedal ergometer fixations are provided, such as e.g. a strap fixation for the test person's foot, calf and shoulders, which can also be adjusted to the height of the test person or patient.

In another preferred embodiment as an arm ergometer, corresponding fixations are provided e.g. for the hand or forearm of the test person or patient.

For measuring the distance of the motion of the drive means, a carbon spring comprising at least one strain indicator is provided parallel to the pneumatic cylinder 21. This way, conclusions can be drawn regarding the motion of the drive means, e.g. the pedaling motion, as a function of the output signal of the strain indicator. This carbon spring is designed such that it exhibits a spring constant over a long spring travel, and the spring is operated in this range of the spring travel.

FIG. 2a shows a schematic view of a piston/cylinder array 7, and FIG. 2b shows a sectional view of this piston/cylinder array 7. By means of an adapter 22, the force range to be applied by the test person or patient can be modified in the ranges described above, preferably depending on whether a patient or a test person is examined. This is done by firmly attaching the piston diameter effective in the cylinder either to the cylinder 21 or the piston 20 using an adapter 22 which encircles the piston 20. Preferably, the adapter 22 is screwed to the part at issue.

FIG. 3 shows the measuring of the distance by means of a rotation angle wheel 32 and a bending beam 31. When the drive means is deflected, the bending beam 31 is deflected and the distance traveled by the drive means is determined. For this purpose, the rotation angle wheel 32 is attached to an eccentric rotating pin 34 used as an axis, and the rotation angle wheel 32 is moved as a consequence of the deflection of the drive means, e.g. the pedal 3, and in turn deflects the bending beam 31. Thus, the bending beam 31, whose one end is firmly attached to a fixing device 30, is deflected. At least one strain indicator 33 is provided at the bending beam 31 such that the deformation of the bending beam 31 is converted to an electronic signal.

The invention also encompasses embodiments combining features from different embodiments described above.

What is claimed is:

1. An ergometer, in particular for examining a test person or patient in a magnetic resonance apparatus, comprising:
   at least one drive means, provided essentially movably,
   at least one pneumatic piston/cylinder array, wherein the drive means is provided for movement at the piston or the cylinder and a pneumatically applied pressure between the piston and the cylinder constitutes a resistance or force for deflecting the drive means by the test person or patient,
   characterized in that
   the resistance or force to set the drive means in motion can be controlled or regulated, in particular during operation, wherein the resistance or the force is regulated or controlled automatically or electronically based on measured signals from a feedback loop during examination of the test person or patient,
   wherein the arrangement furthermore comprises a compressed air inlet and an air vessel provided between the compressed air inlet and the ergometer, and
   wherein the air vessel is designed such that the air pressure applied at the piston/cylinder array can be controlled or regulated and guarantees that no high or short-term load peaks result from counter-pressure when the drive means is deflected.

2. The ergometer according to claim 1, wherein the drive means is a pedal or a handle.

3. The ergometer according to claim 2, wherein the ergometer furthermore comprises strap fixations for foot, calf, and shoulders of the test person or patient.

4. The ergometer according to claim 3, wherein the strap fixation for the shoulders can be adjusted to a height of the test person.

5. The ergometer according to claim 1, wherein the piston/cylinder array comprises a gap of at least 0.02 mm and at most 0.05 mm between the piston and the cylinder.

6. The ergometer according to claim 1, wherein the components of the ergometer consist of non-ferromagnetic materials.

7. The ergometer according to claim 1, wherein the drive means comprises a stop which protects the piston from knocking against a bottom of the cylinder.

8. The ergometer according to claim 1, wherein the force to be applied at the drive means is determined via a measurement of the air pressure in the cylinder or in the compressed air inlet.

9. The ergometer according to claim 1, wherein the modulus of elasticity of the piston is ideally 3,000 N/mm$^2$.

10. The ergometer according to claim 1, wherein a measurement of a distance of the motion of the drive means is carried out with a carbon spring comprising at least one strain indicator which is provided parallel to the pneumatic cylinder.

11. The ergometer according to claim 10, wherein the carbon spring is designed such that it exhibits a spring constant over a long spring travel and the spring is operated in this range.

12. The ergometer according to claim 10, wherein the distance is determined by means of a bending beam which is deflected by the motion of the drive means.

13. The ergometer according to claim 12, wherein a rotation angle wheel is firmly attached to an eccentric rotating pin used as an axis and provided such that it is moved as a consequence of the deflection of the drive means and in turn deflects the bending beam.

14. The ergometer according to claim 12, wherein one end of the bending beam is firmly attached by means of a fixing device and is deflected at a distance thereto.

15. The ergometer according to claim 12, wherein the at least one strain indicator is provided at the bending beam such that deformation of the bending beam is converted to an electronic signal.

16. The ergometer according to claim 1, wherein the drive means is attachable on-center to a body part of the test person or patient to be measured.

17. The ergometer according to claim 1, wherein the force to be applied by the test person or patient is modified by modifying the piston diameter effective in the cylinder by means of an adapter encircling the piston which is attached to either the cylinder or the piston.

18. The ergometer according to claim 1, wherein the force to be applied at the drive means is up to about 600 N for healthy test persons and ideally about 300 N for patients.

19. The ergometer arrangement according to claim 1, wherein the arrangement furthermore comprises a control means whose sensors and accompanying protected cables are provided within an examination chamber of the magnetic resonance apparatus and electronic controls of the control means are located outside of the examination chamber of the magnetic resonance apparatus.

20. The ergometer arrangement according to claim 19, wherein the control means regulates the air pressure at the piston/cylinder array and thus the pressure exerted onto the piston which constitutes the force necessary to be applied by the test person or patient in order to deflect the drive means.

21. The ergometer arrangement according to claim 19 wherein the control means comprises a computer and a computer program for controlling and/or processing acquired data.

22. The ergometer according to claim 1, wherein the force to be applied at the drive means is determined via at least one strain indicator at the piston.

23. The ergometer according to claim 22,
wherein in the area of the strain indicator an diameter of the piston is smaller than in a cylinder guidance.

24. The ergometer according to claim 22,
wherein the piston is hollow at least in the area of the strain indicator.

25. A method for operating an ergometer,
according to claim 1, in the magnetic resonance apparatus, comprising the steps:
providing the at least one movable drive means,
providing the at least one pneumatic piston/cylinder array comprising arranging the drive means at the piston or the cylinder and creating the resistance or force to be overcome by the test person or patient by operating the drive means and providing the pneumatically applied pressure between the piston and the cylinder,
characterized by
controlling and/or regulating the resistance or force necessary to set the drive means in motion, particularly during operation, wherein the step of regulating or controlling the resistance or the force is automatically or electronically, based on the measured signals from the feedback loop during the examination of the test person or patient,
wherein the step of controlling and/or regulating is performed by the ergometer.

26. An ergometer, in particular for examining a test person or patient in a magnetic resonance apparatus, comprising:
at least one drive means, provided essentially movably,
at least one pneumatic piston/cylinder array, wherein the drive means is provided for movement at the piston or the cylinder and a pneumatically applied pressure between the piston and the cylinder constitutes a resistance or force for deflecting the drive means by the test person or patient,
characterized in that;
i) wherein a measurement of a distance of the motion of the drive means is carried out with a carbon spring comprising at least one strain indicator which is provided parallel to the pneumatic cylinder;
ii) wherein the distance is determined by means of a bending beam which is deflected by the motion of the drive means.

27. A method for operating the ergometer
according to claim 2, in the magnetic resonance apparatus, comprising the steps:
providing the at least one movable drive means,
providing the at least one pneumatic piston/cylinder array comprising arranging the drive means at the piston or the cylinder and creating the resistance or force to be overcome by the test person or patient by operating the drive means and providing the pneumatically applied pressure between the piston and the cylinder,
characterized by
forming an air cushion between the piston and the cylinder during operation or when they move relative to each other;
wherein the step of forming the air cushion is implemented by the ergometer.

\* \* \* \* \*